United States Patent
Varma

(10) Patent No.: US 11,090,084 B2
(45) Date of Patent: Aug. 17, 2021

(54) FETUS DELIVERY ASSISTING DEVICE

(71) Applicant: Safe Obstetric Systems Ltd., Brentwood (GB)

(72) Inventor: Rajiv Varma, Shenfield (GB)

(73) Assignee: SAFE OBSTETRIC SYSTEMS LIMITED, Brentwood (GB)

( * ) Notice: Subject to any disclaimer, the term of this patent is extended or adjusted under 35 U.S.C. 154(b) by 0 days.

(21) Appl. No.: 16/192,290

(22) Filed: Nov. 15, 2018

(65) Prior Publication Data

US 2019/0142467 A1    May 16, 2019

(30) Foreign Application Priority Data

Nov. 16, 2017   (GB) .................................. 1718988

(51) Int. Cl.
| | |
|---|---|
| *A61B 17/44* | (2006.01) |
| *A61B 17/42* | (2006.01) |
| *A61B 17/00* | (2006.01) |
| *A61B 90/00* | (2016.01) |

(52) U.S. Cl.
CPC ............ *A61B 17/442* (2013.01); *A61B 17/42* (2013.01); *A61B 2017/00544* (2013.01); *A61B 2017/00557* (2013.01); *A61B 2090/0807* (2016.02)

(58) Field of Classification Search
CPC .................. A61B 17/42; A61B 17/442; A61B 2017/00544; A61B 2017/00557
See application file for complete search history.

(56) References Cited

U.S. PATENT DOCUMENTS

| | | | |
|---|---|---|---|
| 713,708 | A | 11/1902 | Spire |
| 3,106,441 | A | 10/1963 | Harrison et al. |
| 3,480,017 | A | 11/1969 | Shute |
| 4,018,230 | A | 4/1977 | Ochiai et al. |
| 4,207,891 | A | 6/1980 | Bolduc |
| 4,338,943 | A | 7/1982 | Okamoto et al. |
| 4,480,424 | A | 11/1984 | Seldon |
| 5,307,811 | A | 5/1994 | Sigwart et al. |

(Continued)

FOREIGN PATENT DOCUMENTS

| | | |
|---|---|---|
| CN | 2875343 | 3/2007 |
| DE | 10038469 | 2/2002 |

(Continued)

OTHER PUBLICATIONS

Arad et al, Vacuum Extraction at Cesarean Section—Neonatal Outcome, 1986, Journal of Perinatal Medicine, vol. 14, No. 2, pp. 137-140.

(Continued)

*Primary Examiner* — Kathleen S Holwerda
*Assistant Examiner* — Brooke Labranche
(74) *Attorney, Agent, or Firm* — Fish & Richardson P.C.

(57) ABSTRACT

A fetus delivery assisting device (10) for assisting with the birth of a fetus. The device (10) comprises a shaft (16). At one end of the shaft (16) is a rigid base (18) to which an inflatable balloon (12) is mounted. The rigid base (18) and the inflatable balloon (12) are configured to accept a fetal head. The inflatable balloon (12) is configured to displace the fetal head from a pelvic cavity when inflated. The shaft (16) is configured for manipulating the inflatable balloon (12) to displace the fetal head from the pelvic cavity.

27 Claims, 15 Drawing Sheets

(56) References Cited

U.S. PATENT DOCUMENTS

| | | | |
|---|---|---|---|
| 5,308,327 | A | 5/1994 | Heaven et al. |
| 6,056,772 | A * | 5/2000 | Bonutti ............... A61B 17/0401 606/139 |
| 6,104,941 | A * | 8/2000 | Huey ................... A61B 5/0448 600/338 |
| 6,355,047 | B1 | 3/2002 | Wallace et al. |
| 7,018,392 | B2 | 3/2006 | Hudson et al. |
| 7,713,282 | B2 * | 5/2010 | Frazier ............... A61B 17/0057 606/200 |
| 8,556,913 | B2 | 10/2013 | Varma |
| 9,055,973 | B2 | 6/2015 | Varma |
| 10,010,345 | B2 | 7/2018 | Mackovic Basic et al. |
| 2002/0010441 | A1 | 1/2002 | Horkel |
| 2002/0183779 | A1 | 12/2002 | Vigil |
| 2004/0059289 | A1 | 3/2004 | Alvarez |
| 2008/0249534 | A1 * | 10/2008 | Gruber ................... A61B 1/303 606/119 |
| 2009/0312807 | A1 | 12/2009 | Boudreault et al. |
| 2014/0163578 | A1 * | 6/2014 | Yaari ....................... A61B 17/42 606/122 |
| 2016/0100861 | A1 | 4/2016 | Parys et al. |
| 2016/0135843 | A1 | 5/2016 | Chinchoy et al. |
| 2017/0065298 | A1 | 3/2017 | Harris et al. |
| 2018/0206886 | A1 * | 7/2018 | Beaven ................ A61B 17/442 |

FOREIGN PATENT DOCUMENTS

| | | |
|---|---|---|
| WO | WO 2001/010493 | 2/2001 |
| WO | WO 2005/030064 | 4/2005 |
| WO | WO 2006/085045 | 8/2006 |
| WO | WO 2016/186922 | 11/2016 |

OTHER PUBLICATIONS

Bader et al, Maternal and Fetal Catecholamines and Uterine Incision-to-Delivery Interval During Elective Cesarean, Apr. 1990, Obstetrics & Gynecology, vol. 75, No. 4, pp. 600-603.

Blickstein, Difficult Delivery of the Impacted Fetal Head During Cesarean Section: Intraoperative Disengagement Dystocia, 2004, Journal of Perinatal Medicine, vol. 32, No. 6, pp. 465-469.

Demott et al, The Green Bay Cesarean Section Study: II. The Physician Factor as a Determinant of Cesarean Birth Rates for Failed Labor, Jun. 1992, American Journal for Obstetrics and Gynecology, vol. 166, Part 1, pp. 1799-1810.

Hager et al, Complications of Cesarean Deliveries: Rates and Risk Factors, Feb. 2004, American Journal of Obstetrics and Gynecology, vol. 190, Issue 2, pp. 428-434.

Mukhopadhyay et al., "Evaluation of Patwardhan's Technic—a four year study in a rural teaching hospital," The Journal of Obstetrics and Gynecology of India, vol. 55, No. 3, May/Jun. 2005, pp. 244-246.

Murphy et al, Early Maternal and Neonatal Morbidity Associated with Operative Delivery in Second Stage of Labour: A Cohort Study, Oct. 13, 2001, The Lancet, vol. 358, pp. 1203-1207.

Fasubaa et al, Delivery of the Impacted Head of the Fetus at Caesarean Section After Prolonged Obstructed Labour: A Randomized Comparative Study of Two Methods, Jul. 2002, Journal of Obstetrics and Gynaecology, vol. 22, No. 4, pp. 375-378.

* cited by examiner

FETUS DELIVERY ASSISTING DEVICE

CROSS-REFERENCE TO RELATED APPLICATIONS

This application claims priority to GB Patent Application Number 1718988.7 filed Nov. 16, 2017, the content of which is incorporated herein by reference in its entirety.

BACKGROUND OF THE INVENTION

The present invention relates to a fetus delivery assisting device.

The average rate of fetal delivery by caesarean section in, for example, the UK is around 25%. In the UK, around half of caesarean sections are emergency and about half are elective. Deeply engaged head, when the head of the fetus is deeply engaged in the maternal pelvic cavity, occurs in around 10% to 20% of emergency caesarean sections and some elective caesarean sections. This can lead to a difficult delivery of the fetal head. Maternal and fetal complications can arise due to this difficulty.

During delivery by caesarean section of a deeply engaged fetal head, pushing the fetal head through the vaginal route is known. However, this technique can cause direct trauma to the fetus and delay in delivery. A high rate of maternal trauma and infections has also been reported while using this technique. Other known techniques are reverse breech extraction, which is often difficult and traumatic unless the operator is familiar with it.

A device known as the Fetal Pillow device invented by the inventor of the present patent application has been in use for a few years. The Fetal Pillow device includes an inflatable balloon on a flexible foldable base. In use, the base and balloon are folded by hand and inserted by hand through the vaginal opening. The base is then unfolded and placed underneath a fetal head that is deeply engaged in the maternal pelvic cavity. The balloon of the device is then inflated when filled with fluid, which elevates the fetal head and helps disengage it from the maternal pelvic cavity.

Such a device and method are also described in U.S. Pat. Nos. 8,556,913 and 9,055,973. FIG. 1 is an illustration from these patents.

FIG. 1 illustrates a device including an inflatable portion 1 in the shape of a balloon. The inflatable portion is mounted on a plate 2 by sticking to it by appropriate adhesive. The plate 2 has a hole in the middle to allow connecting tubing 4 to be attached to the inflatable portion for its inflation. It is disclosed that the edges of the plate need to be either soft or rounded to be least traumatic to the maternal tissues. The tubing is attached by using a connector 3. The base plate has a simple mechanism which allows it to be folded in the middle along the short axis. This can be in the form of a thinner area in the plate itself. The device includes a syringe 7 to push in fluid to inflate the inflatable portion. A stopcock 6 is also provided to be opened to allow a user to push in fluid (or not).

BRIEF SUMMARY OF THE INVENTION

The inventors of the present disclosure have appreciated that users of the Fetal Pillow device and device described in U.S. Pat. Nos. 8,556,913 and 9,055,973 can use the device incorrectly, for example, insert it upside down. Therefore, it can fail to achieve the desired elevation of the fetal head. The inventors of the present disclosure have appreciated that it may be difficult to insert the Fetal Pillow device and device described in U.S. Pat. Nos. 8,556,913 and 9,055,973 and place it in the desired location in the pelvic cavity under the fetal head; it is difficult to place it in a correct position at times. The inventors of the present disclosure have appreciated that the Fetal Pillow device and device described in U.S. Pat. Nos. 8,556,913 and 9,055,973 may be expelled if not placed in a correct position below the fetal head.

This disclosure describes a fetus delivery assisting device and method that is simple to insert and remove through a maternal uterine incision or vaginally. This disclosure describes a device that may be accurately placed underneath a fetal head deeply in the pelvic cavity.

The invention in its various aspects is defined in the independent claims below to which the references should now be made. Optional features are set forth in the dependent claims.

An example arrangement of the present disclosure is described in more detail below and takes the form of a fetus delivery assisting device for assisting with the birth of a fetus. The device comprises an inflatable balloon configured to displace a fetal head from a pelvic cavity when inflated; and a shaft attached to the balloon. The shaft is configured for insertion and removal of the balloon.

An example of an embodiment of the disclosure is a surgical device in the form of a balloon device for elevating the fetal head or other parts in the pelvis, particularly when the fetal head is deeply engaged in the pelvic cavity. This may be carried out before a caesarean section. It may also be used to elevate the breech before performing an external cephalic version. This is a procedure to turn a fetus from a breech position into a head-down position. The device can also be used when a cord prolapse has occurred. Cord prolapse is when the umbilical cord comes out of the uterus with or before the presenting part of the fetus.

Broadly, the fetus delivery assisting device comprises a balloon that inflates only in an upward direction from between the pelvic cavity and the fetal head. The balloon is attached to a firm lower portion or base. The lower portion has a fixed, rigid or non-foldable curved shape to fit the pelvic cavity on one side and the fetal head on the other side. Attached to this firm base is a long-curved shaft that has a handle at its distal end. The shaft has markings or indicators on it. The handle allows easy and accurate insertion of the device and also makes it easy to remove the device after use. The balloon is attached to tubing that allows a user to inflate the balloon using a syringe or a mechanical or powered pump using fluid, such as gas.

The rigid base and shaft is curved to fit the curvature of the maternal pelvic cavity, and the curve of the fetal head. This prevents the obstetrician from inserting the device upside down, and also allows the device to more easily achieve the desired elevation of the fetal head. In plan view, the base may be round, oval or elongate in shape. In cross section, the base may be flat, have an angle, such as a V shape cross section, or be a curve.

The rigid base may comprise surface features such as a plurality of projections such as ridges configured to increase friction between the device and the pelvic cavity to make it less likely that the device will be expelled from the pelvic cavity during use.

The provision of a curved shaft allows for easy insertion and removal of the device.

The shaft may comprise indicators such as markings or notches to indicate to an obstetrician the depth of insertion. The indicators allow for accurate placement of the device beneath the variable position of the fetal head.

The elongated handle may comprise an insertion end. The insertion end may comprise an enlarged portion, with thickness substantially larger than that of the rest of the elongated handle, which improves the obstetricians grip on the device and allows for easier insertion and removal.

The length of the elongated handle may vary, and may be longer in the case of an obese patient.

The device may further comprise an inflation tube, optionally comprising a two-way tap, to allow for inflation and deflation of the balloon by inserting and releasing fluid from the balloon. The two-way tap may be locked to create a seal, to prevent escape of fluid from the balloon. The fluid may be any biocompatible fluid, for example, a liquid such as saline, glucose solution, Ringer's lactate (also known as sodium lactate solution or Hartmann's solution, which is a mixture of sodium chloride, sodium lactate, potassium chloride and calcium chloride in water) or a gas or gases such as carbon dioxide. The fluid may be delivered by any suitable pressurizing device, such as a syringe, pump, blood pressure cuff, pressure balloon, piston cylinder or the like.

The device may comprise a mechanical or electronic attachment that could allow the physician to accurately measure the elevation of the fetal head, and judge the amount of fluid required before performing a caesarean section. The mechanical or electronic attachment may do this by measuring the distance between the balloon's base and uppermost point or dome, and relating this to the level of expansion of the balloon.

In an aspect of the present disclosure, there is provided a fetus delivery assisting device for assisting with the birth of a fetus, the device comprising: a shaft, at one end of the shaft is a rigid base to which an inflatable balloon is mounted; the rigid base and the inflatable balloon are configured to accept a fetal head; the inflatable balloon is configured to displace the fetal head from a pelvic cavity when inflated; and the shaft is configured for manipulating the inflatable balloon to displace the fetal head from the pelvic cavity.

In another aspect of the present disclosure, there is provided a method of assisting in the birth of a fetus, the method comprising: inserting, between a pelvic cavity and a fetal head, an inflatable balloon mounted to a rigid base arranged at one end of a shaft such that the fetal head is accepted into the rigid base and the uninflated inflatable balloon; and inflating the inflatable balloon and manipulating the inflatable balloon using the shaft to displace the fetal head from the pelvic cavity.

In another aspect of the present disclosure, there is provided a kit of parts comprising: a fetus delivery assisting device for assisting with the birth of a fetus, the device comprising: a shaft attachable to a rigid base to which an inflatable balloon is mountable; the rigid base and the inflatable balloon are configured to accept a fetal head; the inflatable balloon is configured to displace the fetal head from a pelvic cavity when inflated; and the shaft is configured for manipulating the inflatable balloon to displace the fetal head from the pelvic cavity.

In another aspect of the present disclosure, there is provided a fetus delivery assisting device for assisting with the birth of a fetus, the device comprising: an inflatable balloon configured to displace a fetal head from a pelvic cavity when inflated; and at least one shaft attached to the balloon.

This arrangement provides for ready insertion and removal of the device and/or manipulation of the device to help release the fetal head from the maternal pelvic cavity.

The at least one shaft may comprise an insertion shaft configured for insertion and removal of the balloon. The insertion shaft may comprise a handle at one end. The handle may comprise a widening of the shaft. This allows the device to be gripped well by a user. The insertion shaft may have a curve shape. This provides allows for ready insertion and removal of the device. The device may comprise an inflation tube for providing fluid to inflate the inflatable balloon. The inflation tube may be attached to the at least one shaft. In this way, the inflation tube is less of an obstruction to a user of the device. Kinking and, therefore, blocking of the tube is also prevented. The inflation tube may comprise a two-way tap. The at least one shaft may comprise at least one indicator for indicating insertion depth of the device. This provides a simple, but effective way to measure insertion depth. The at least one shaft may comprise a plurality of indicators for indicating insertion depth of the device. The device may further comprise a rigid base. The inflatable balloon may be mounted to the rigid base. The rigid base and the inflatable balloon may be configured to accept a fetal head. The rigid base may be concave. This prevents the obstetrician from inserting the device upside down, and also allows the device to more easily achieve the desired elevation of the fetal head. The rigid base may comprise surface features configured to provide friction between the rigid base and the pelvic cavity. The surface features may be located on a surface of the base opposite to the inflatable balloon. The surface features may comprise a plurality of projections projecting outwardly from the surface of the base opposite to the inflatable balloon. The plurality of projections may be spaced apart over the surface of the base opposite to the inflatable balloon. The surface features may comprise ridges. This arrangement provides good grip or friction of the device and, in particular, the base of the device with the balloon in the pelvic cavity. This helps to prevent the device from being expelled from the pelvic cavity during use. The inflatable balloon may comprise a plurality of chambers. This provides a good shape to release the fetal head from the maternal pelvic cavity. The plurality of chambers may be arranged beside one another. The plurality of chambers may be arranged on top of one another. The balloon wall may comprise a top portion that is less distensible than another portion of the balloon wall. This provides a good shape to release the fetal head from the maternal pelvic cavity. The inflatable balloon may be inflated to a pressure between about 6 kPa and about 400 kPa. The device may further comprise a fluid path, such as a fluid channel or tube, for introducing fluid between the pelvic cavity and the fetal head. The fluid may be a lubricant. This helps in releasing the fetal head from the pelvic cavity. The fluid tube may be attached to the shaft. In this way, the fluid tube is less of an obstruction to a user of the device. Kinking and, therefore, blocking of the tube is also prevented. The at least one shaft may comprise a manipulation shaft configured to assist in manipulating the device. This extra handle allows the device to be manipulated to push the fetal head manually if the delivery proves difficult despite the inflated balloon. The manipulation shaft may be detachably attachable to the device.

In another aspect of the present disclosure, there is provided a fetus delivery assisting device for assisting with the birth of a fetus, the device comprising: a rigid base and an inflatable balloon mounted to the base; the rigid base and the uninflated inflatable balloon being configured to accept a fetal head; and the inflatable balloon being configured to displace the fetal head from a pelvic cavity when inflated.

This prevents the obstetrician from inserting the device upside down, and also allows the device to more easily achieve the desired elevation of the fetal head.

In another aspect of the present disclosure, there is provided a fetus delivery assisting device for assisting with the birth of a fetus, the device comprising: an inflatable portion comprising a plurality of chambers configured to control inflation of the inflatable portion to displace a fetal head from a pelvic cavity when at least one of the plurality of chambers is inflated.

This provides a good shape and reduces risk of balloon distortion during inflation to release the fetal head from the maternal pelvic cavity.

In another aspect of the present disclosure, there is provided a fetus delivery assisting device for assisting with the birth of a fetus, the device comprising: an inflatable balloon configured to displace a fetal head from a pelvic cavity when inflated; wherein the device comprises a fluid path to introduce fluid between the pelvic cavity and the fetal head.

This aids in releasing the fetal head from the maternal pelvic cavity.

In another aspect of the present disclosure, there is provided a method of assisting in the birth of a fetus, the method comprising: inserting an inflatable balloon between a pelvic cavity and a fetal head using a shaft attached to the balloon; and inflating the inflatable balloon to displace the fetal head from the pelvic cavity.

In another aspect of the present disclosure, there is provided a method of assisting in the birth of a fetus, the method comprising: inserting, between a pelvic cavity and a fetal head, an inflatable balloon mounted to a rigid base such that the fetal head is accepted into the rigid base and the uninflated inflatable balloon; and inflating the inflatable balloon to displace the fetal head from the pelvic cavity.

In another aspect of the present disclosure, there is provided a method of assisting in the birth of a fetus, the method comprising: inserting, between a pelvic cavity and a fetal head, an inflatable portion comprising a plurality of chambers; and inflating at least one of the chambers to inflate the inflatable portion to displace the fetal head from the pelvic cavity.

In another aspect of the present disclosure, there is provided a method of assisting in the birth of a fetus, the method comprising: inserting an inflatable balloon between a pelvic cavity and a fetal head; and manipulating the inflatable balloon using a shaft attached to the balloon to displace the fetal head from the pelvic cavity.

In another aspect of the present disclosure, there is provided a method of assisting in the birth of a fetus, the method comprising: inserting an inflatable balloon between a pelvic cavity and a fetal head; and delivering fluid between the pelvic cavity and the fetal head.

In another aspect of the present disclosure, there is provided a kit of parts comprising: a fetus delivery assisting device for assisting with the birth of a fetus, the device comprising an inflatable balloon configured to displace a fetal head from a pelvic cavity when inflated; and a manipulation shaft, wherein the manipulation shaft is detachably attachable to the device to assist in manipulating the device.

This application also incorporates the entirety of PCT Application No. PCT/GB2018/053313 filed Nov. 15, 2018 by reference.

BRIEF DESCRIPTION OF THE SEVERAL VIEWS OF THE DRAWINGS

The invention will be described in more detail, by way of example, with reference to the accompanying drawings in which.

Like features of the drawings are denoted by like reference numerals.

DETAILED DESCRIPTION OF THE INVENTION

An example fetus delivery assisting device 10 and method for assisting with the birth of a fetus will now be described will reference to FIGS. 2 to 7.

Figure 1:
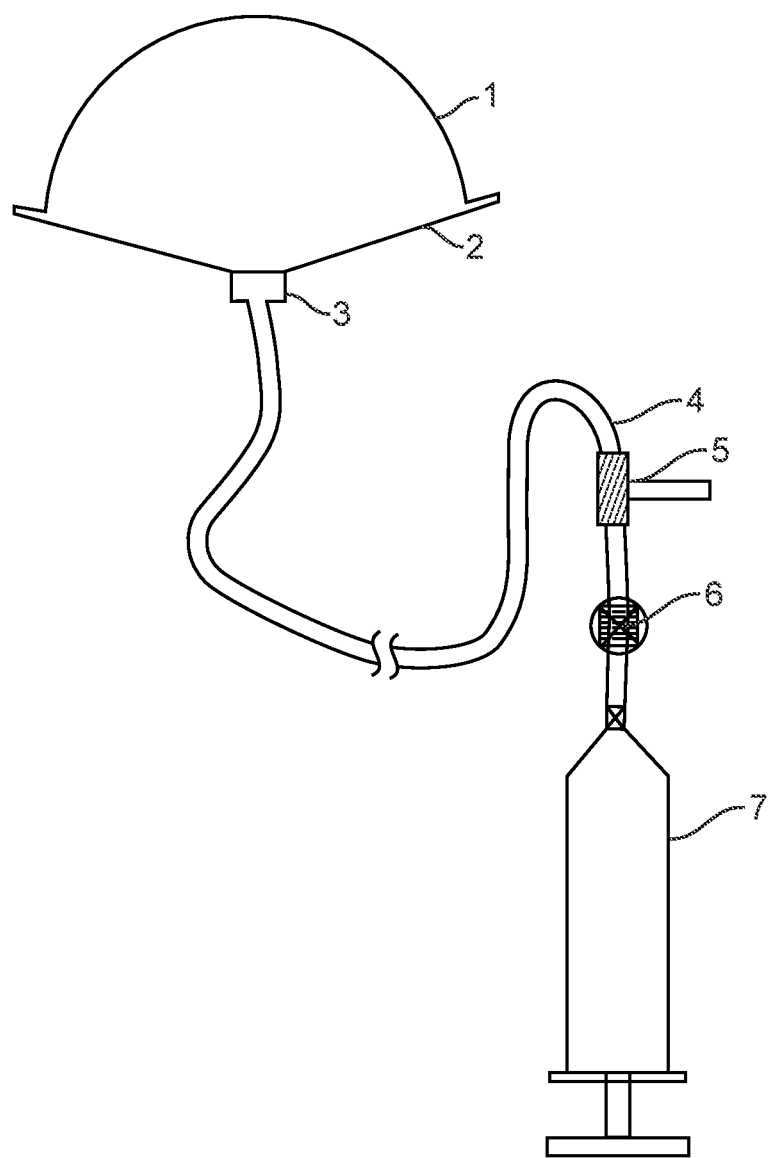
FIG. 1 (prior art) is side view of a known fetus delivery assisting device.
Figure 2:
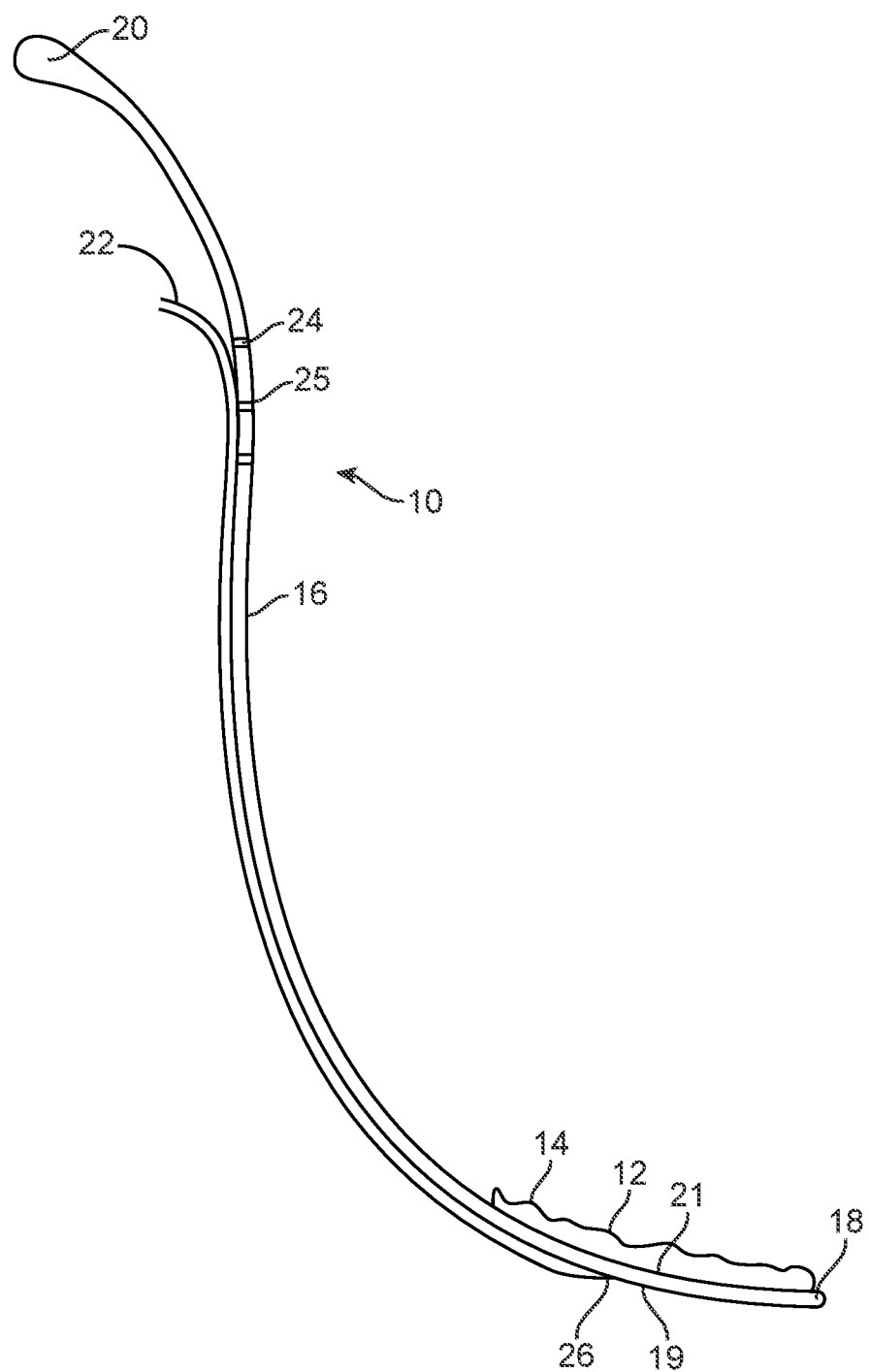
FIG. 2 is a side view of a fetus delivery assisting device embodying an aspect of the present invention in an uninflated state.

Referring first to FIG. 2, the fetus delivery assisting device 10 has an inflatable balloon 12 shown uninflated in FIG. 2. The balloon has a wall 14 of distensible biocompatible material. The inflatable balloon is attached to a rigid shaft 16. The shaft is made from biocompatible material. At one end (the proximal end or insertion end) of the shaft is a rigid base 18 to which the balloon is attached. Significantly, the base is not configured to fold; it cannot fold. The base has a fixed, concave shape. The curvature of the base is such that the base conforms to the curvature of a fetal head. At the other end of the shaft (the distal end) is a handle 20. This is formed by a widening and thickening of the shaft. The shaft has a curve shape. From the side, the balloon device is broadly an S shape or sigmoid shape. In the example of FIG. 2, the S shape is relatively flat, however, the curvature of the S shape may be tighter at one end, or both ends. The radius of curvature of the two curved portions of the S shape are similar to each other in the illustrated balloon device, however, one end of the S shape may have a larger, or much larger, radius of curvature than the other. The device has a tube 22 or inflation tube for providing fluid to inflate the inflatable balloon. The tube extends from the balloon and along the shaft so that it is directed towards the handle or distal end of the shaft. The inflation tube is attached to the shaft (this is explained further below with reference to FIG. 3). The rigid base has a through hole 26 through it through which the tube passes to the balloon. The tube can also be connected to the balloon without going through the base. The tube is attached to the shaft.

The inflation tube 22 has a two-way tap (not illustrated in FIG. 2). The tap allows fluid to pass through the inflation tube to the balloon 12 or from the balloon out through the inflation tube depending on the direction the tap is turned.

The shaft 16 includes a region with a plurality of indicators 24 spaced apart along part of its length. In this example, the indicators are markings or lines that extend around the circumference of the shaft. The indicators are located in a region that reflects an approximate position of a distance to the pelvic cavity where the balloon 12 is to be located and where the shaft enters the body. The center of the region reflects typical extremes of the position of the shaft when the balloon is correctly located in the pelvic cavity. Thus, when the device 10 is in use, the indicators indicate to a user the depth that the device has been inserted.

Figure 3:
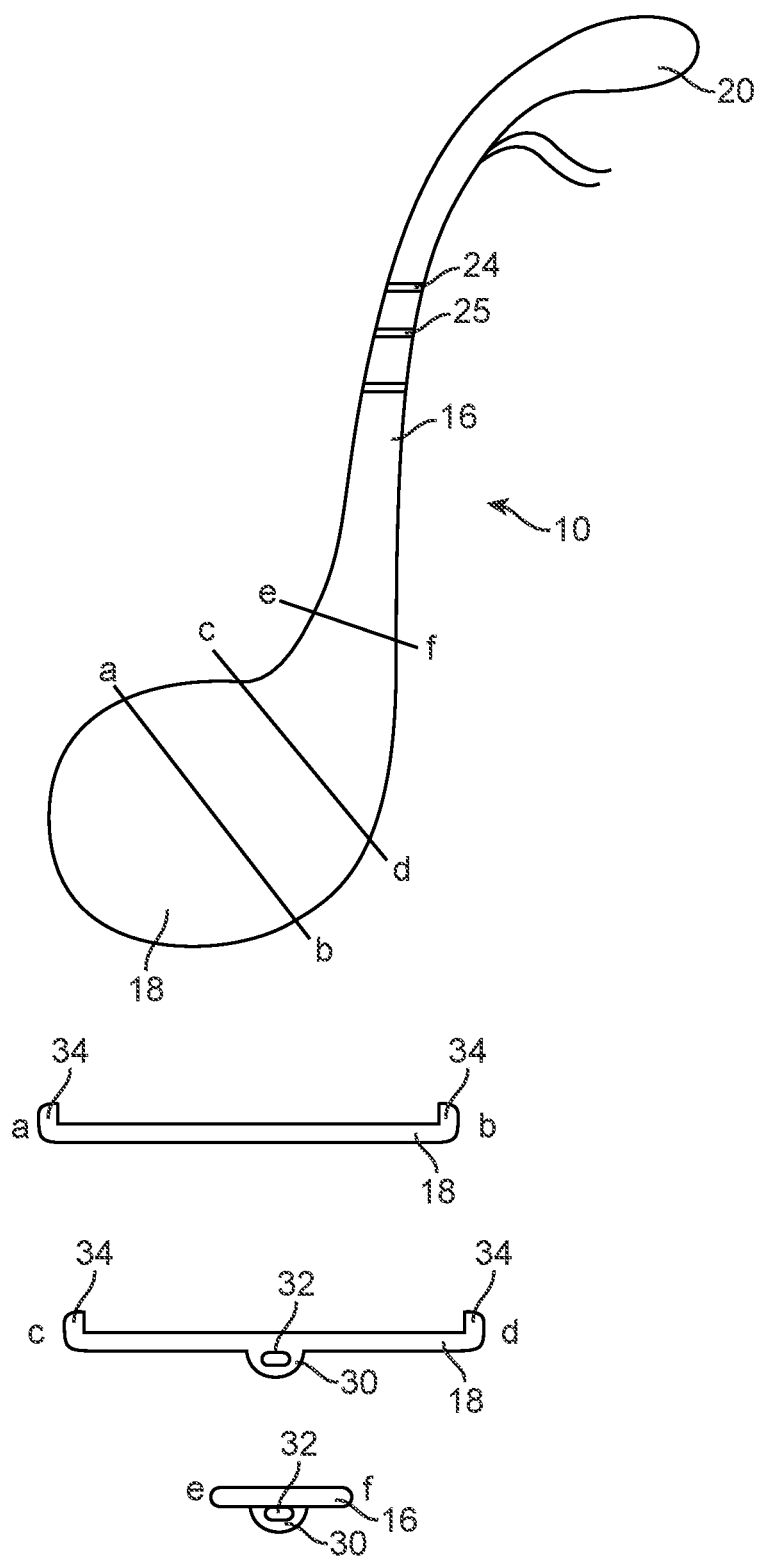
FIG. 3 is an isometric view of part of the fetus delivery assisting device of FIG. 2 and cross-sectional views through portions of it.

FIG. 3 illustrates the shaft 16 and base 18 of the fetus delivery assisting device 10. A portion of the base towards the shaft (cross section c-d of FIG. 3) and the shaft towards the base (cross section a-b) includes a channel 32 defined by an outer wall 30. The channel extends along this portion of the base and shaft. The inflation tube (not shown in FIG. 3) passes through the channel. Thus, the inflation tube is attached to the shaft and base by the channel. As shown by cross section a-b of FIG. 3, the channel does not extend as far as the free end of the base. The channel does not extend to the free end of the shaft towards the handle.

As also illustrated in FIG. 3, the outer edges 34 of the base 18 project outwardly from the surface of the base (cross sections a-b and c-d of FIG. 3) on the opposite side as the supports 30 from the same side as the balloon 12 is located. They hold the balloon 12 to the base as explained below with reference to FIG. 4. The width of the base varies along its length from its free end to the shaft end. From the free end, the base widens to a maximum width in the middle of the base (cross section a-b). The base then narrows towards the shaft of the device (cross section c-d). This enables the base to conform to the shape of the fetal head. It also helps hold the balloon to the base as explained below.

Figure 4A:
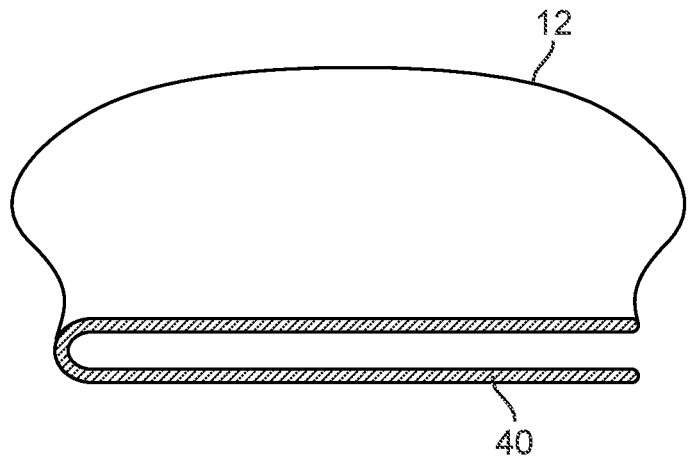
FIG. 4A is a cross sectional view from the side of a portion of the fetus delivery assisting device of FIG. 2.
Figure 4B:
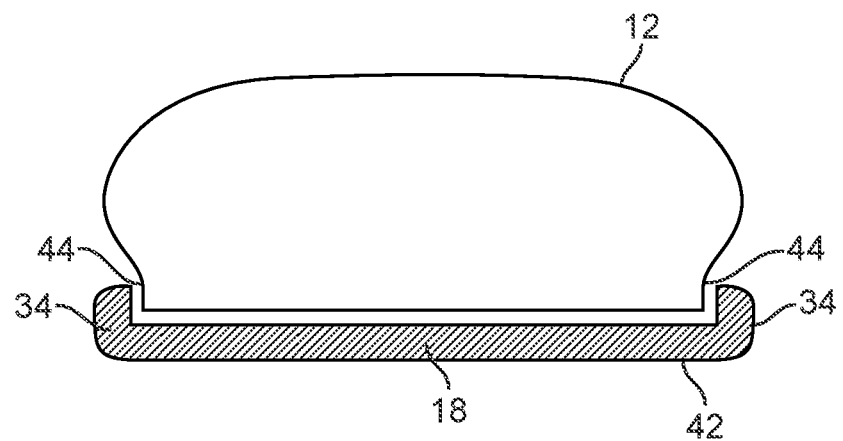
FIG. 4B is a cross sectional view from the front of an alternative arrangement of the portion of the fetus delivery assisting device of FIG. 4A.

FIG. 4A illustrates the balloon 12 fixed to the base 18 when looking from a side of the fetus delivery assisting device 10. The balloon has a double layer 40 at the bottom into which the base or plate is inserted. This layer 40 takes the form of a resilient clip. In use, the clip is pushed on to the free end 42 of the base. In other words, the attachment is by inserting the base plate into the double layer at the base of the balloon. Alternative arrangements may be provided to hold the balloon 12 to the base 18. Another example is illustrated in FIG. 4B. In the arrangement of FIG. 4B, the balloon 12 is attached to the surface of the base or plate 18. The balloon narrows at its base end with straight or vertical sides. The base includes projections 34 that project from the outer edge of the base from the surface of the base towards the balloon. The sides 44 of the balloon engage with the projections 34 from the outer edges of the base 34. As described above with reference to FIG. 3, the base widens and then narrows from its free end towards the handle and, in this way together, the balloon is held or attached to the base by these features.

The rigid base 18 of the fetus delivery assisting device 10 has surface features (not illustrated). The surface features are projections that project outwardly from the lower surface 19 of the rigid base, the other side of the rigid base to the balloon 12 and away from the balloon side 21. In this example, the surface features are ridges that extend across the rigid base, in this example, across the width of the base. The projections narrow towards their free end. In this example, the free end of the projections extend away from the insertion or proximal end of the device. The surface features may be made from the same material as the base or a different material. This arrangement provides good grip or friction of the device and, in particular, the base of the device with the balloon in the pelvic cavity. This helps to prevent the device from being expelled from the pelvic cavity during use.

Figure 5:
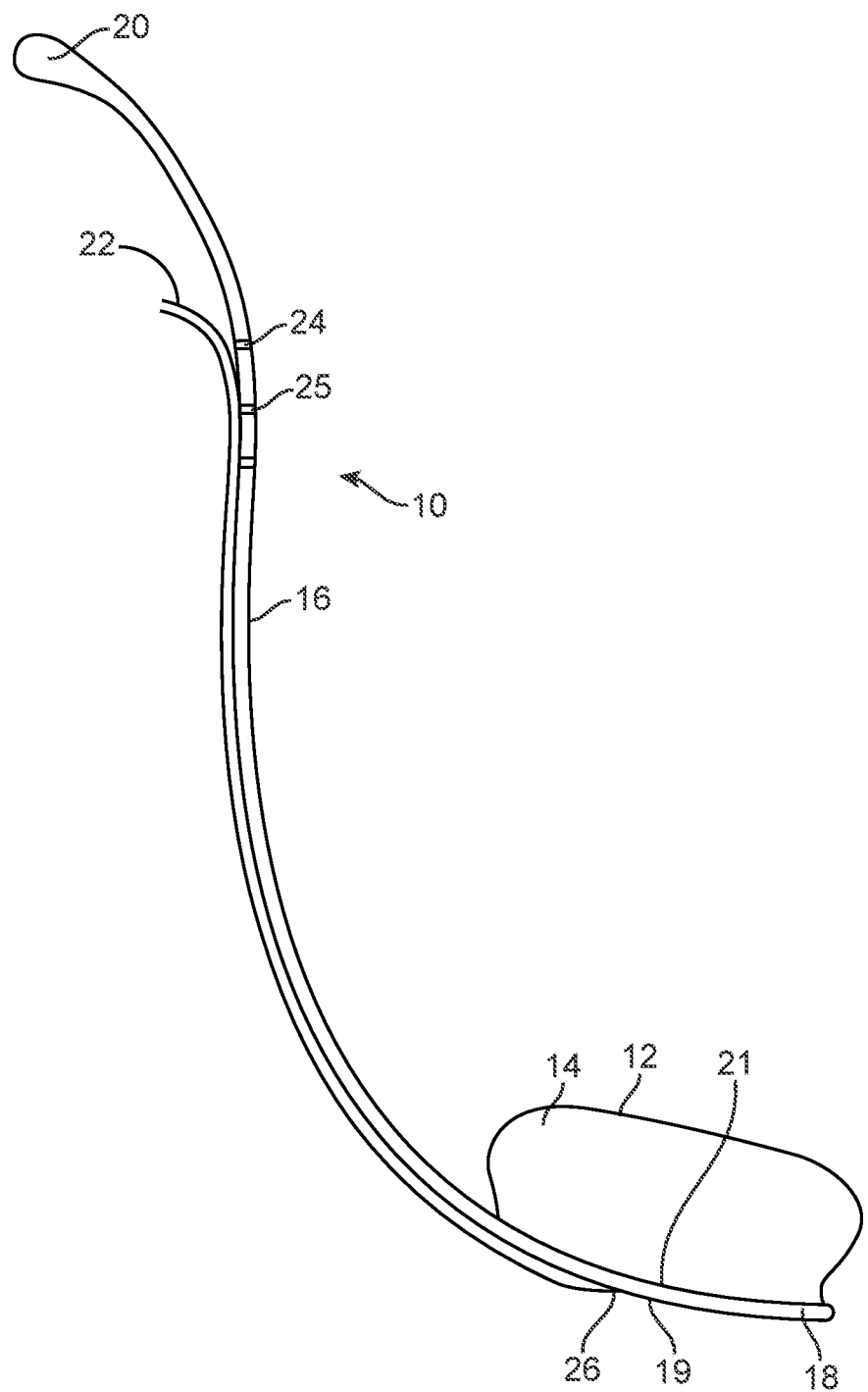
FIG. 5 is a side view of the fetus delivery assisting device of FIG. 2 in a partially inflated state.

FIG. 5 shows the same fetus delivery assisting device 10 as that of FIG. 2 and like features have been given like reference numerals. The balloon 12 of the device of FIG. 2 is shown partially inflated such that an outer portion of the wall 14 is spaced from the base 18 of the device, such that, in use, when located between a fetal head and pelvic cavity it displaces the fetal head from the pelvic cavity as explained in more detail below. The maximum balloon inflation volume may be between 100 and 500 cubic centimeters (cc).

Figure 6:
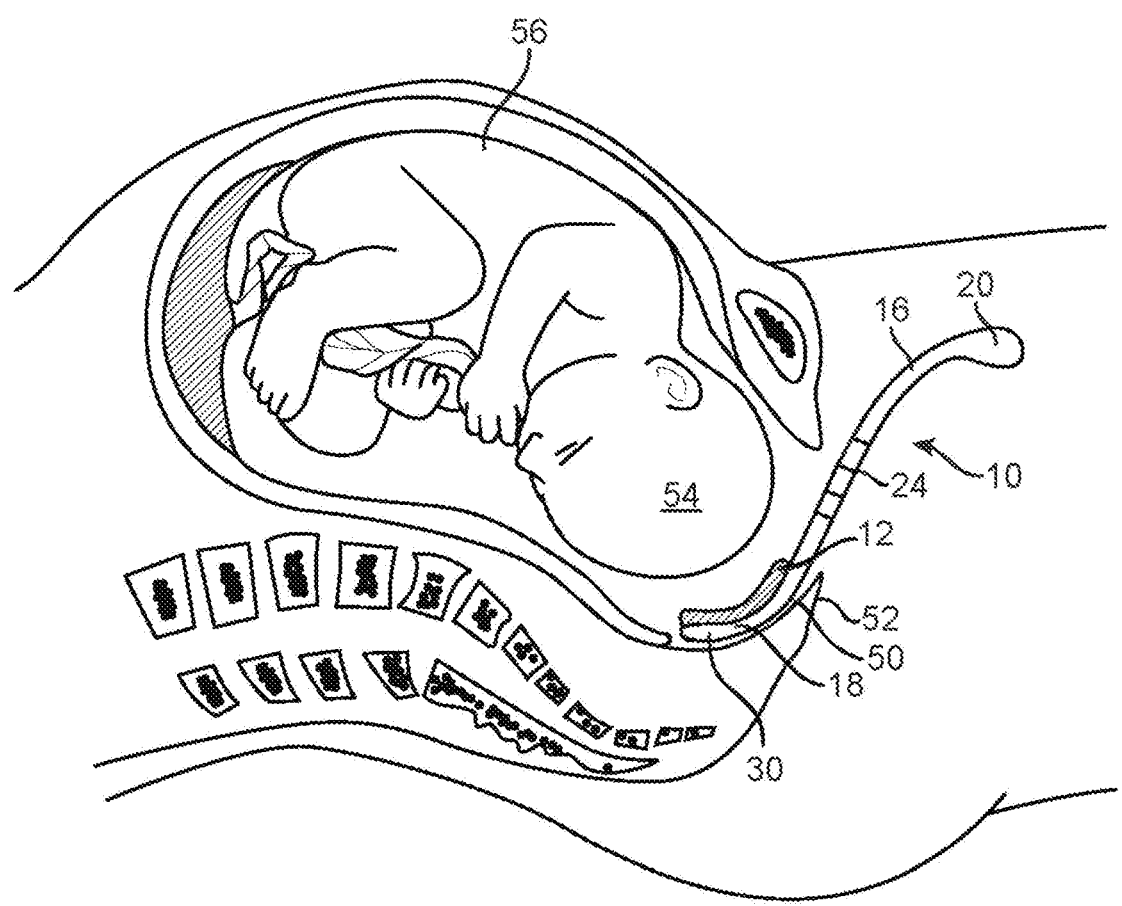
FIG. 6 is a cross sectional view of the fetus delivery assisting device of FIG. 2 in its deflated state in use in the pelvic cavity.
Figure 7:
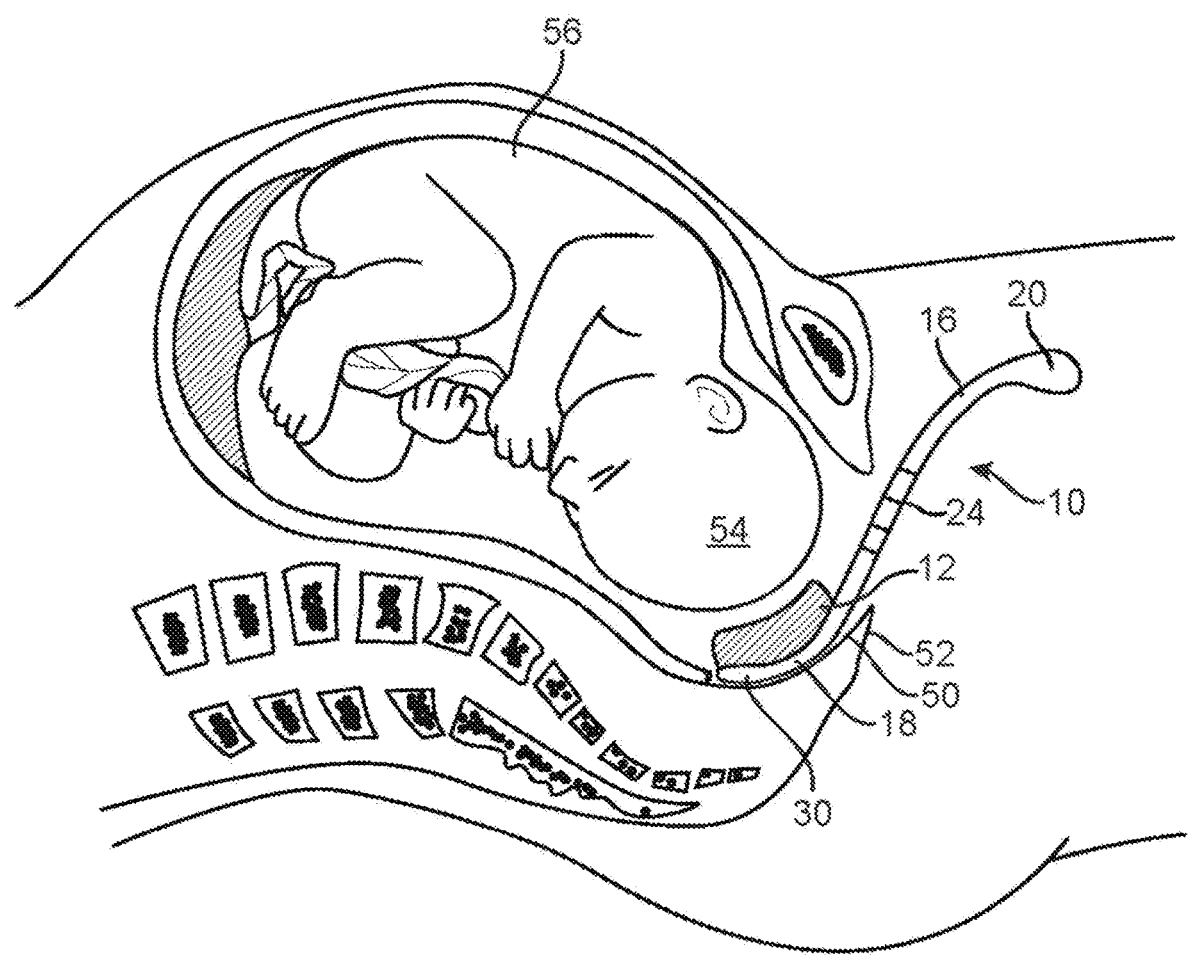
FIG. 7 is a cross sectional view of the fetus delivery assisting device of FIG. 2 in its inflated state in use in the pelvic cavity.

FIGS. 6 and 7 illustrate the fetus delivery assisting device 10 in use in a pelvic cavity 50. In this example, the device is inserted vaginally, but as stated above it may also be inserted through a maternal uterine incision.

Broadly, in use, the fetus delivery assisting device 10, with the balloon 12 uninflated, is inserted through a vaginal opening 52 and then between the pelvic cavity 50 and a fetal head 54 using the shaft 16 attached to the balloon such that the fetal head is accepted into the rigid base 18 and the uninflated inflatable balloon. The balloon is then inflated to displace the fetal head from the pelvic cavity.

Referring first to FIG. 6, in use, the handle 20 of the device 10 is held by a user such as an obstetrician (not shown). The base end, insertion end or proximal end 30 of the device is inserted into the vagina 52 of the mother by the obstetrician with the balloon is in its fully uninflated state. The base end of the device, in the uninflated state, is inserted between the pelvic cavity 50 and the fetal head 54 and such that the curvature of the base 18 fits the curvature of the pelvic cavity and the fetal head. The spaced apart markings or indicators 24 on the shaft 16 indicate to the obstetrician the depth that the device has been inserted. In this example, there are three markings. The middle of the three markings 25 indicates the expected ideal positioning of the device.

Referring now to FIG. 7, when the device 10 is in the correct position between the fetal head 54 and the pelvic cavity 50 as indicated by the indicators 24, the balloon 12 is inflated with a fluid by passing the fluid through the inflation tube 22 (not shown in FIG. 7). In this example, the fluid is saline. The balloon may be inflated to give a pressure in the balloon of between 50 mm Hg (about 6 kPa) and 3000 mm Hg (about 400 kPa). The fluid is delivered into the inflation tube by a suitable pressurizing device (not shown) and when the two-way tap (not shown in FIGS. 6 and 7) is in a position to allow fluid flow to pressurize the balloon. In this example, the pressurizing device is a syringe. A mechanical or electronic attachment, which in this example is a pressure gauge (not shown), indicates to the obstetrician how much fluid must be inserted to achieve a certain amount of lift to the fetal head and to release it from the pelvic cavity. As an alternative to a syringe as the pressurizing device, the pressurizing device may be an electronically controlled pump, such as using a pulsatile method for a slow rise in pressure. Alternative mechanisms for speed filling may be provided.

Once the obstetrician has inflated the balloon 12 and the fetal head 54 has been released or dislodged from the pelvic cavity, the fetus 56 may be readily delivered.

Once the fetal head has been released from the pelvic cavity, the fetus deliver assisting device 10 is removed. First, the balloon 12 is deflated by releasing the fluid through the inflation tube 22 (not shown in FIGS. 6 and 7). This is done by the user turning the two-way tap such that the saline is drained from the balloon. The user then pulls the device out from the vagina 52 by the handle 20. This arrangement allows for easy removal of the device.

Figure 8:
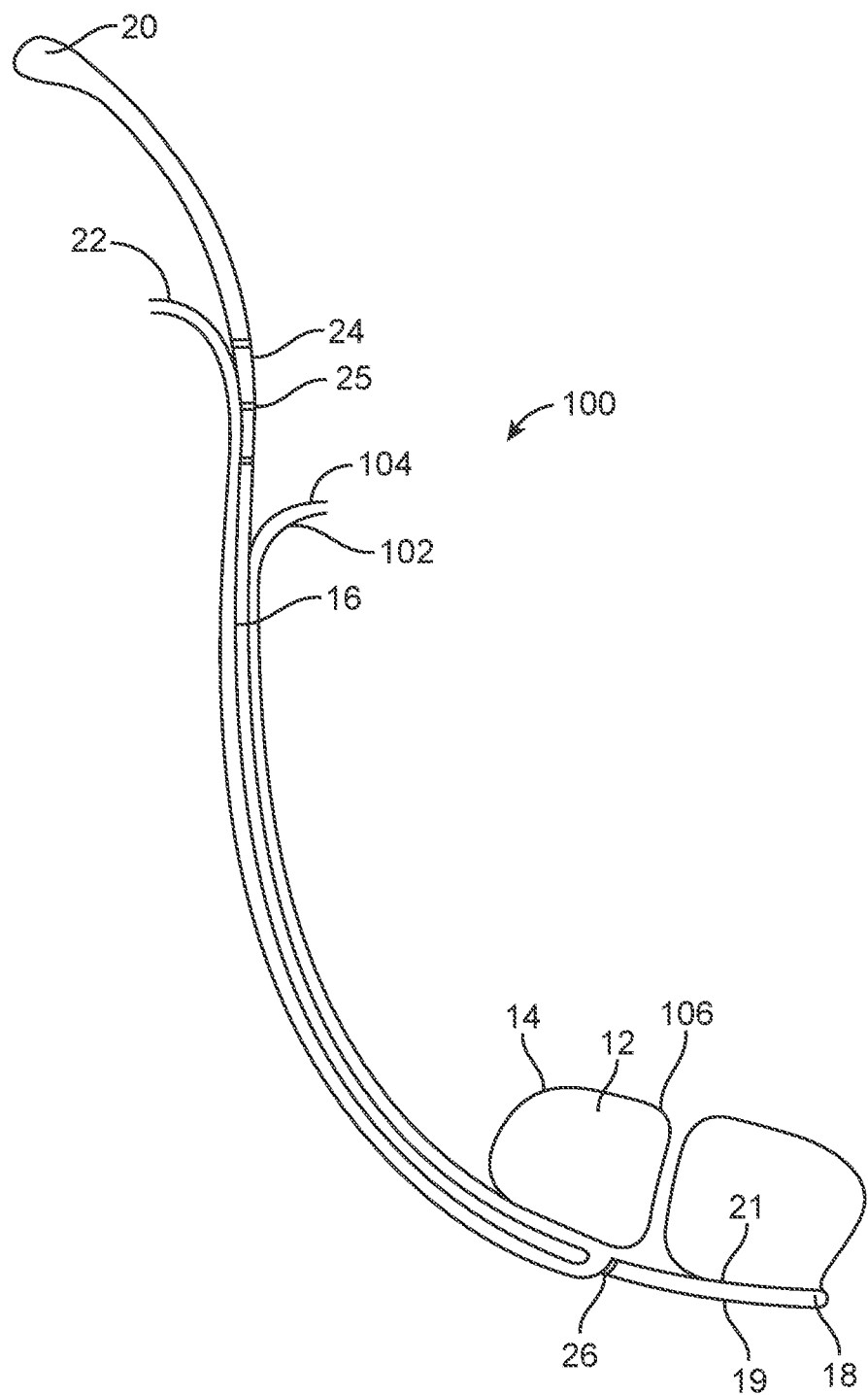
FIG. 8 is a cross sectional view of another fetus delivery assisting device embodying an aspect of the present invention.

The fetus delivery assisting device 100 illustrated in FIG. 8 is the same in most respects to the arrangement illustrated in FIGS. 2 to 5, and like features have been given like reference numerals.

The fetus delivery assisting device 100 of FIG. 8 includes a tube or fluid tube 102 for introducing or instilling fluid and particularly liquid between the pelvic cavity and the fetal head. The fluid tube is attached to the shaft 16. It is attached to the balloon side of the shaft. In other words, it is on the other side of the shaft to the inflation tube 22. The fluid tube extends along the shaft from its free end 104 and through the balloon. The tube terminates at the outer surface 106 of the balloon. Thus, in this example, the balloon is annular, ring shape or doughnut shape when inflated. In this way, fluid can be introduced or instilled on to the outer surface of the balloon in contact with the fetal head. In this example, the fluid is a lubricant. This arrangement further eases release of the fetal head by helping to equalize the pressure from behind the fetal head with the surrounding maternal pelvic cavity.

Figure 9:
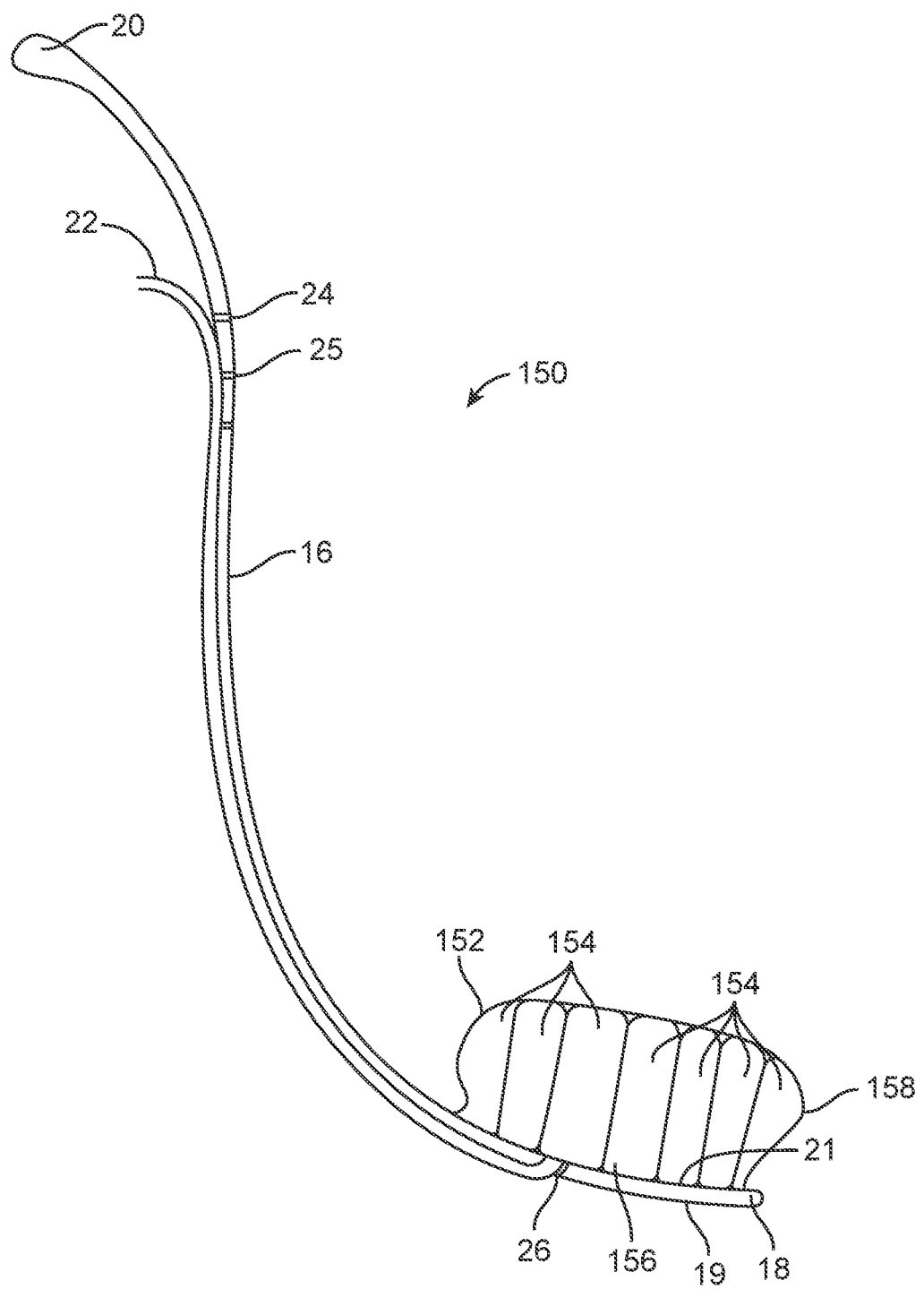
FIG. 9 is a cross sectional view of a yet further fetus delivery assisting device embodying an aspect of the present invention.

The fetus delivery assisting device 150 illustrated in FIG. 9 is the same in most respects to the arrangement illustrated in FIGS. 2 to 5, and like features have been given like reference numerals.

Rather than including a single balloon 12 of the device 10 of FIGS. 2 to 5, the device 150 of FIG. 9 includes an inflatable portion 152 that has a plurality of chambers or cavities 154 configured to control inflation of the inflatable portion to displace a fetal head from a pelvic cavity when at least one or all of the plurality of chambers is inflated. In this example, there are seven chambers. There may be, for example, two or more cavities, an odd number of chambers more than one, or between 3 and 11 chambers. In this example, the chambers are arranged beside one another along the base 18 or horizontally. There is a central chamber 156 and the chambers 154 around it are each annular, ring shape or doughnut shape chambers one inside the other. The chambers 154 are covered with a cover 158. The cover forms a continuous surface over the chambers. The balloon chambers are inflatable and deflatable with a single inflation tube 22. Through holes through walls of the chambers allow fluid to move between them. The use of a plurality of chambers provides good strength to the inflatable portion, and assists in maintaining the inflatable portion's shape during use.

As an alternative to the shapes described above, the chambers may be a cylindrical or sausage shape located either beside each other or on top of one another or both.

The inflatable portion (either a single balloon or made up of a plurality of chambers) may be distensible or not distensible (fixed volume) when inflated.

In an alternative arrangement to that of FIG. 9, rather than the fetus delivery assisting device having chambers 154 that are arranged beside one another along the base 18 or horizontally, the fetus delivery assisting device may have a plurality of chambers arranged on top of one another or vertically.

Figure 10:
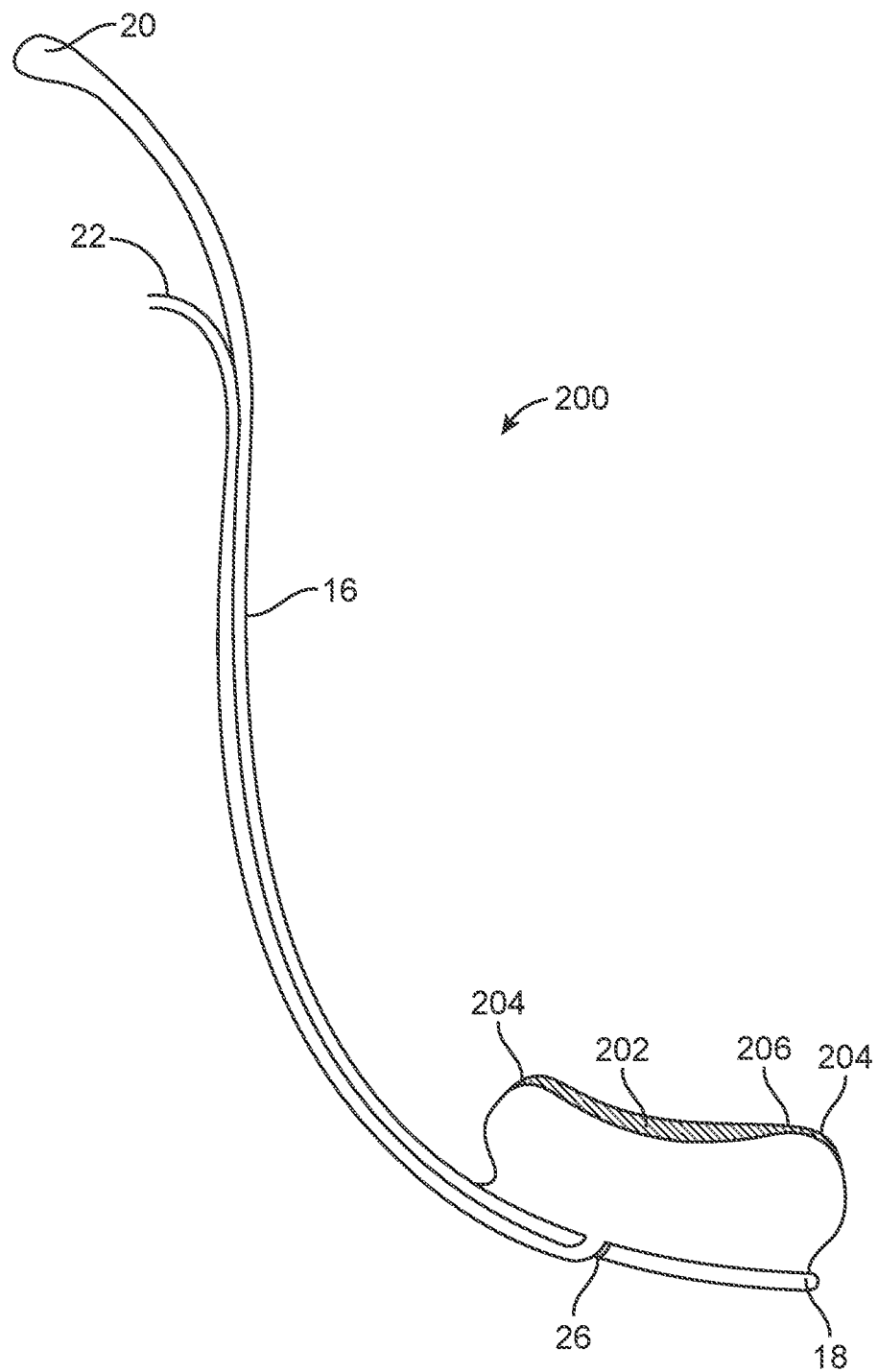
FIG. 10 is a cross sectional view of another fetus delivery assisting device embodying an aspect of the present invention.

The fetus delivery assisting device 200 illustrated in FIG. 10 is the same in most respects to the arrangement illustrated in FIGS. 2 to 5, and like features have been given like reference numerals.

The balloon 12 of the fetus delivery assisting device 200 of FIG. 10 has a portion 202 of increased balloon wall thickness which decreases the distensibility of that portion in order to adapt the shape of the balloon when inflated. In this example, the portion of increased thickness is the middle or central portion of the balloon, which enables the outer edge or edges 204 of the balloon to distend further than this middle or central portion. Thus, in this example, when the balloon is inflated as shown in FIG. 10, the upper side 206 of the balloon, which is in contact with the fetal head (not shown in FIG. 10) when in use, mimics the curve shape of the base 18 to conform well to the shape of the fetal head or, in other words, to mould to the fetal head shape.

Figure 11:
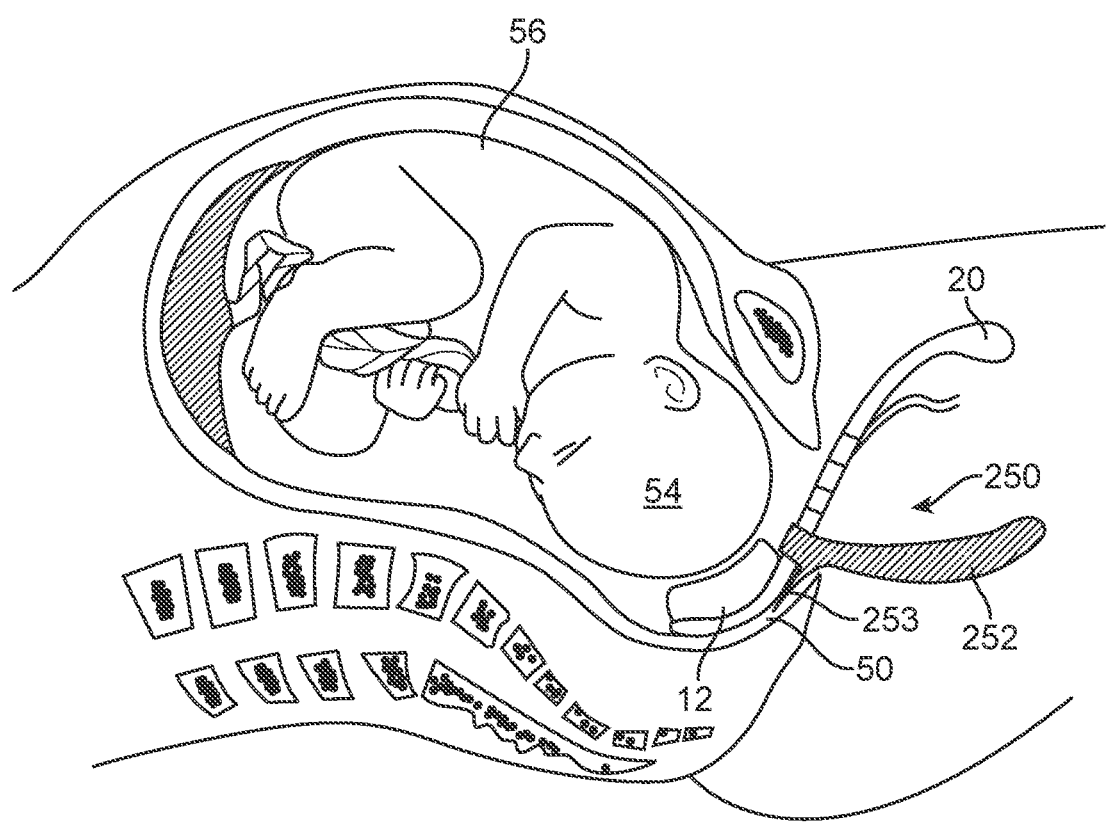
FIG. 11 is a cross sectional view of a fetus delivery assisting device embodying an aspect of the present invention in its inflated state in use in the pelvic cavity.

The fetus delivery assisting device 250 illustrated in FIG. 11 is the same in most respects to the arrangement illustrated in FIG. 10, and like features have been given like reference numerals.

The fetus delivery assisting device 250 of FIG. 11 has a second handle 252. In this example, the second handle is attached to the shaft. The second handle is attached to the shaft by a clamp. The second handle provides a lever such that the user can apply upward pressure to the fetal head 54 to further assist with delivery of the fetus 56. For example, in the situation where the balloon 12 is fully inflated but has not pushed the fetal head far enough for delivery. In other words, an extra handle is provided that can be attached to the device to help to push the fetal head manually if the delivery proves difficult despite the inflated balloon.

In addition, a wedge 253 may be inserted beneath the fetus delivery assisting device 250 to create a strong pivot point for the device so that it can act as a lever to ease the fetal head from the pelvic cavity if inflation of the balloon 12 is not sufficient.

Figure 12:
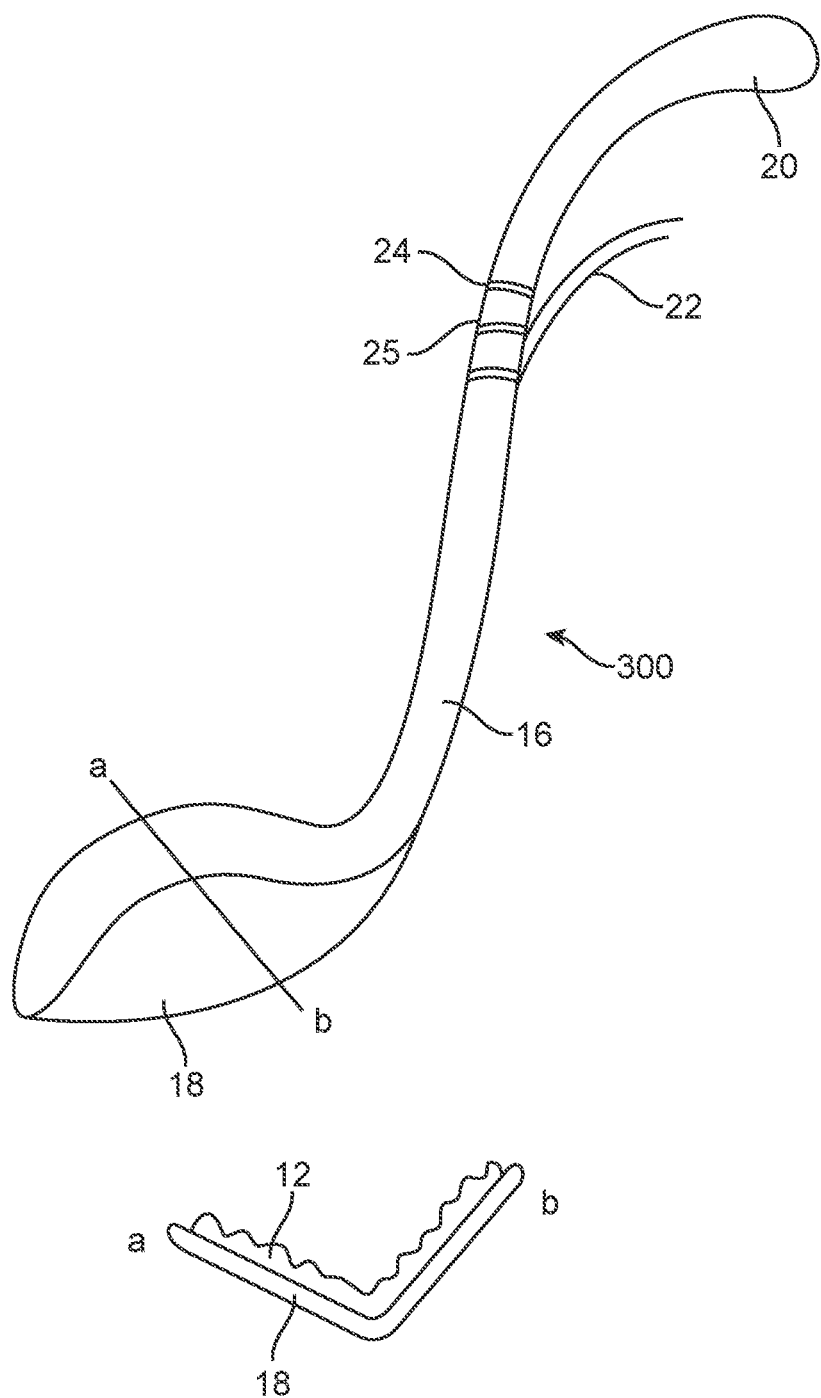
FIG. 12 is a side view of a fetus delivery assisting device embodying an aspect of the present invention and a cross sectional view of part of the fetus delivery assisting device.

The fetus delivery assisting device 300 illustrated in FIG. 12 is the same in most respects to the arrangement illustrated in FIGS. 2 to 5, and like features have been given like reference numerals.

Figure 13:
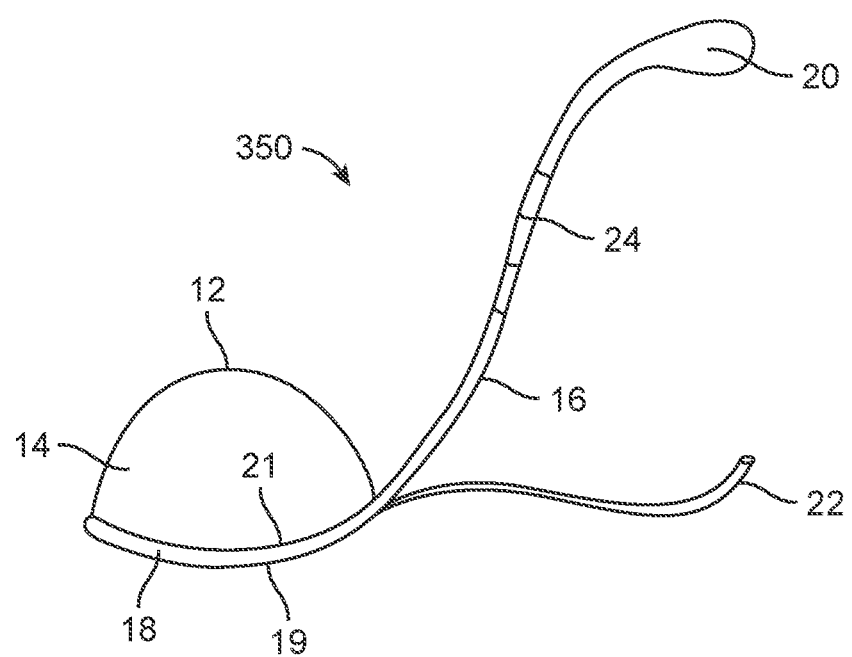
FIG. 13 is a side view of a fetus delivery assisting device embodying an aspect of the present invention in an inflated state.

The fetus delivery assisting device 300 of FIG. 12 has a different shape base plate to the example illustrated with respect to FIGS. 2 to 5. Significantly, the base plate 18, illustrated by cross section a-b of FIG. 12, has a fixed angle or V-shape cross section along the longitudinal axis of the base. The partial fold in the middle or V shape of the base plate enables easy insertion of the fetus delivery assisting device The fetus delivery assisting device 350 illustrated in FIG. 13 is the same in most respects to the arrangement illustrated in FIGS. 2 to 7, and like features have been given like reference numerals. The fetus delivery assisting device 350 of FIG. 13 differs from the arrangement of FIGS. 2 to 7 in that the inflation tube 22 is not attached to the shaft 16. The inflation tube extends outwardly away from the balloon 12. This is a simple arrangement.

Various forms of the base or plate have been described above with reference to the Figures. As an alternative to the arrangements described, the plate or base may be flat and rigid or flexible or partly folded for ease of insertion.

As described above, broadly, the fetus delivery assisting device comprises a balloon that inflates only in an upward (i.e., normal) direction from between the pelvic cavity and the fetal head. The balloon is attached to a lower portion or base that will be relatively more firm than the balloon. In some variations, the base can have a degree of flexibility to conform to a wall of the pelvic cavity. In some variations, the base is flattened. The lower portion can have a curved shape to fit the pelvic cavity on one side and the fetal head on the other side. Variations of the base can include a fixed, rigid or non-foldable base. As the balloon inflates and engages the fetal head, the base presses against a wall of the cavity to ensure that the balloon expands in a direction that is normal to the base.

The device can also include a shaft attached to the base. In one example, the shaft is a long curved shaft that has a handle at its distal end. The shaft can have markings or indicators that provide information to the physician as to the placement or depth of the device within the body. The handle allows easy and accurate insertion of the device and also makes it easy to remove the device after use. Moreover, the handle allows for positioning of the base and balloon from outside of the body. The balloon can be attached to lumen that allows a user to inflate the balloon using a pressure device such as a syringe or a mechanical or powered pump using fluid, such as gas. Variations of the device can include pressure devices that are affixed to a portion of the shaft 16, handle 20, or device 10. The lumen can comprise a tubing affixed to/in the shaft or a passage within the shaft.

The shaft and base can be respectively curved to fit the curvature of the maternal pelvic cavity and the curve of the fetal head.

The device may further comprise an inflation tube as illustrated in FIG. 3. FIG. 3 is an isometric view of the fetus delivery device of FIG. 2 including cross sectional views through portions of the device along lines a-b, c-d and e-f. The view is of a device with a balloon removed. The fetus delivery device optionally comprises a two-way tap or valve, to allow for inflation and deflation of the balloon by inserting and releasing fluid from the balloon. As described above, the fetus delivery assisting device 100 of FIG. 8 includes an additional tube or fluid tube 102 for introducing or instilling fluid and particularly liquid between the pelvic cavity and the fetal head. The fluid tube can be attached to the shaft 16 (or can comprise a lumen through the shaft) and ultimately leads to the balloon side of the shaft. In other words, it delivers fluid to the fetal head.

As described above, rather than including a single balloon 12 of the device 10 of FIGS. 2 to 5, the device 150 of FIG. 9 includes an inflatable portion 152 that has a plurality of chambers or cavities 154 configured to control inflation of the inflatable portion to displace a fetal head from a pelvic cavity when at least one or all of the plurality of chambers is inflated. Variations of the device include balloon chambers that are inflatable and deflatable or collapsible with a single inflation tube 22. Alternatively, additional fluid lumens can be used for different chambers. The walls of the chambers can be fluidly coupled to allow fluid to move between chambers. As an alternative to the shapes described above, the chambers can have any number of shapes. For example, the chambers may be a cylindrical or sausage shape located either beside each other or on top of one another or both.

As described above, the balloon 12 of the fetus delivery assisting device 200 of FIG. 10 has a portion 202 of increased balloon wall thickness which decreases the distensibility of that portion. Such a configuration alters a shape of the balloon when inflated.

After the fetal head has been released from the pelvic cavity, the fetus delivery assisting device 10 is removed. First, the balloon 12 is deflated or collapsed by releasing the fluid through the inflation tube 22. For example, such a release can be performed by using a valve or two-way tap that drains fluid from the balloon. The user can then pull the device out from the vagina 52 using the handle 20. This arrangement allows for easy removal of the device.

The example or variation of a fetus delivery assisting device 10 described above with reference to FIG. 2 has an expandable member, such as an inflatable balloon 12. The variation of a fetus delivery assisting device of FIG. 2 shows the balloon 12 uninflated to prepare for positioning of the device. The depth of the device is thin enough so that it can be inserted into the tight space underneath the fetal head. Moreover, the expandable member can comprise any structure that can lift the fetal head from the base as described herein.

The example fetus delivery assisting device 10 described above with reference to FIG. 2 has an expandable member, such as an inflatable balloon 12, and the balloon has a distensible wall. An impacted fetal head is located tight to the maternal pelvis and so there is no space for the balloon to expand to the sides of the fetal head. In a variation, a non-distensible fixed volume balloon may be provided.

Variations of the device can include a rigid base or a base that is rigid relative to the balloon or expandable member. Moreover, variations of the base can include a deformable or flexible base that allows conformation to a wall of the uterine cavity as the expandable member expands.

Variations of the base include configurations that do not fold. However, alternate variations of the base allow folding during packaging or preparation of the device.

Figure 15:
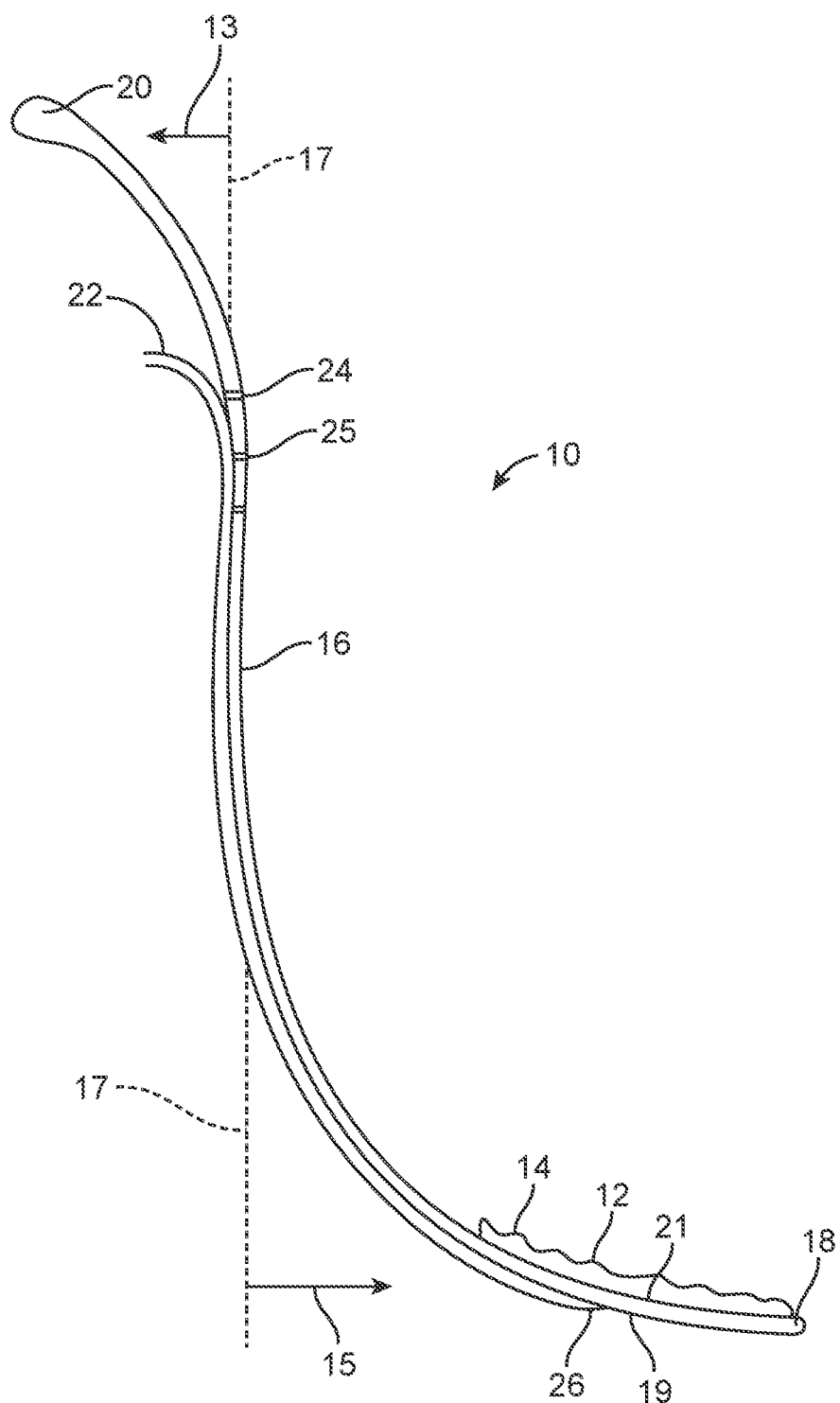
FIG. 15 is a side view of a fetus delivery assisting device embodying an aspect of the present invention in an uninflated state.

In the variation illustrated in FIG. 2 and described with reference to FIG. 15, a side view of the device shows an S shape or sigmoid shape. However, alternate shapes are within the scope of this disclosure. FIG. 15 is the same in most respects to FIG. 2 and like features have been given like reference numerals. As illustrated in FIG. 15, the first end of the shaft 16 (e.g., the handle 20) extends in a first direction 13 away from an axis 17 of the shaft 16 while the base 18 extends in a second direction 15 away from the axis 17. It is noted that the axis 17 of the shaft is illustrated so that the curvature or deviation of first end 20 and base 18 of the device is more pronounced at the ends of the shaft 16. In variations, the first direction 13 and second direction 15 will be in opposite directions (i.e., 180 degrees). However, variations of the device can include first and second directions that extend along opposite sides of the axis 17 as shown, but are not limited to 180 degrees.

As described above, the device can have a tube 22 or inflation tube for providing fluid to inflate the inflatable balloon. Alternatively, a lumen can be incorporated into the handle 16 and fluidly coupled to the balloon 12 and fluid source (not shown).

The rigid base can have a through hole 26 in which the tube is fluidly coupled to the balloon. The tube can also be connected to the balloon without going through the base.

As described above, FIG. 4A illustrates a variation of the device where a balloon 12 is fixed to the base 18 using a resilient clip. Alternatively, or in addition, the balloon can be adhered or otherwise joined to the base.

Figure 14:
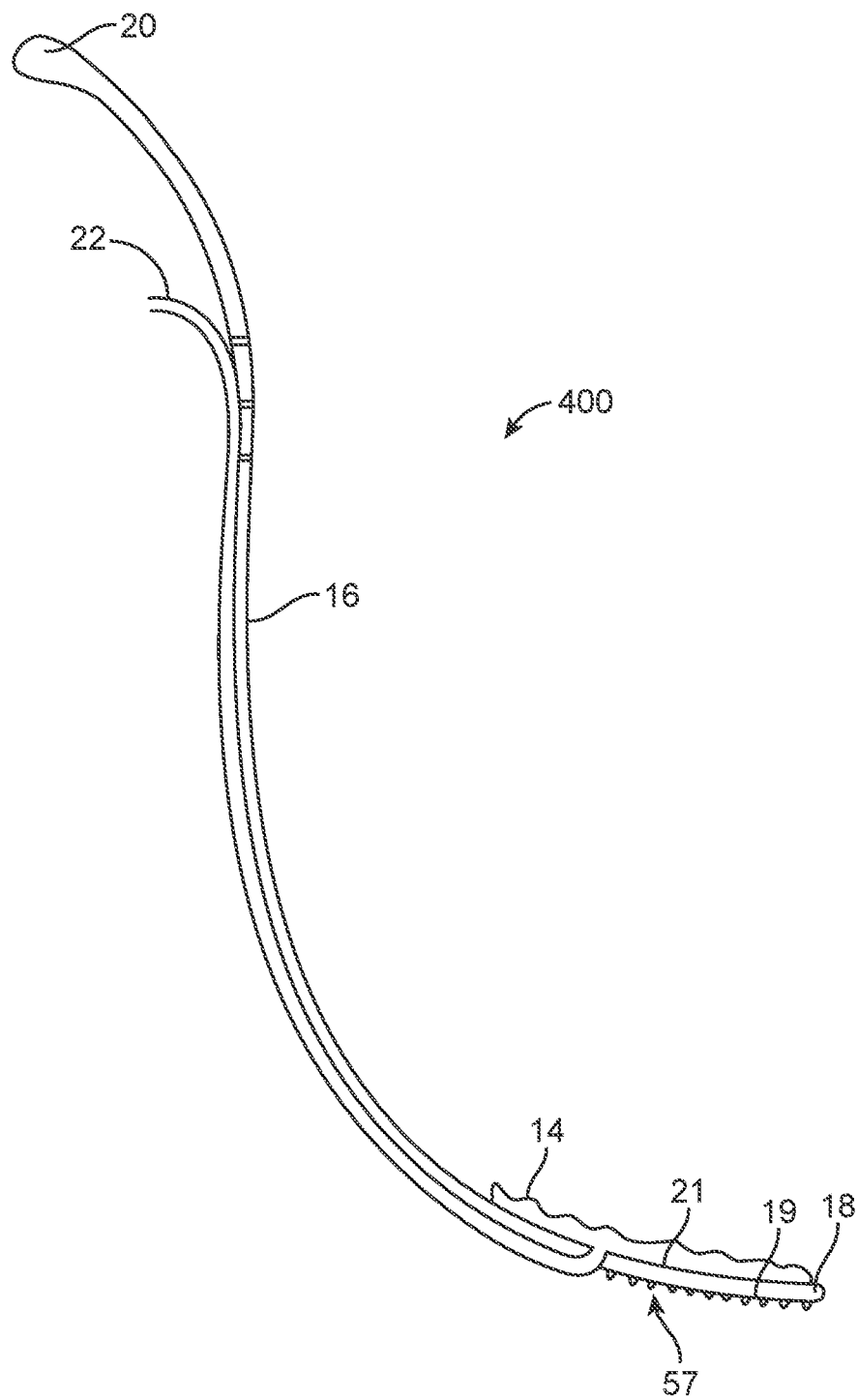
FIG. 14 is a side view of another fetus delivery assisting device embodying an aspect of the present invention in an uninflated state.

As described above, the rigid base 18 of the fetus delivery assisting device 10 can have surface features. This is illustrated in FIG. 14. The fetus delivery assisting device 400 of FIG. 14 is the same in most respects to the fetus delivery assisting device 10 of FIG. 2 and like features have been given like reference numerals. As illustrated in FIG. 14, the surface features can include a roughed texture or a plurality of protrusions or projections on the rigid base that project outwardly from the lower surface 19 of the rigid base and away from the balloon side 21. In other words, an inferior or back side of the base opposite to the expandable member is configured to provide friction between the base and the pelvic wall. The projections on the base reduce the risk of movement and dislodgement.

As mentioned above, the maximum balloon inflation volume may be between 100 and 500 cubic centimeters (cc). Variations of the device can include a maximum balloon inflation volume between 100 and 500 cubic centimeters (cc). However, alternate variations are within the scope of this disclosure.

With reference to the fetus delivery assisting device 300 of FIG. 12, as described above, the base plate 18 has a fixed angle or V-shape cross section along the longitudinal axis of the base. In this variation, the balloon expands normally to the angled legs of the V-shape.

Embodiments of the present invention have been described. It will be appreciated that variations and modifications may be made to the described embodiments within the scope of the present invention.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

I claim:

1. A device for assisting in delivery of a fetus from a pelvic cavity, the device comprising:
 a rigid shaft extending between a first end and a second end, the first end of the shaft extending in a first direction away from a longitudinal axis of the shaft and configured for manipulating the device to adjust a head of the fetus within the pelvic cavity, the second end of the shaft having a fixed arcuate shape;
 a flattened base at the second end of the shaft and extending in a second direction away from the longitudinal axis of the shaft, where the second direction is opposite to the first direction, the flattened base having a width that extends transversely beyond a width of the shaft, where the flattened base comprises a fixed shape;
 an expandable member coupled to the flattened base, the expandable member extending radially outward from the flattened base in the second direction;
 an inflation lumen fluidly coupled to the expandable member; and
 wherein the flattened base is configured for positioning between a fetal head of the fetus and a wall of the pelvic cavity when the expandable member is in a collapsed configuration, and wherein the flattened base is rigid relative to the expandable member such that expansion of the expandable member engages the flattened base against the wall of the pelvic cavity causing the expandable member to expand in a normal direction from the base to further displace the fetal head away from the wall of the pelvic cavity.

2. The device of claim 1, wherein the expandable member is distensible or non-distensible.

3. The device of claim 1, where an entirety of the flattened base is rigid such that it cannot fold.

4. The device of claim 1, where the flattened base is rigid such that the flattened base maintains the fixed shape as the expandable member expands.

5. The device of claim 1, further comprising a handle portion at the first end of the shaft.

6. The device of claim 5, where the handle portion has a width wider than the width of the shaft.

7. The device of claim 1, wherein the first direction comprises an arcuate shape such that the first end of the shaft extends arcuately relative to the longitudinal axis of the shaft.

8. The device of claim 7, wherein a side profile of the device comprises an s-shape.

9. The device of claim 1, wherein the inflation lumen extends within the shaft.

10. The device of claim 1, wherein the inflation lumen extends externally to the shaft.

11. The device of claim 1, further comprising a two-way valve in fluid communication with the inflation lumen.

12. The device of claim 1, further comprising at least one indicator on the shaft, the at least one indicator configured to provide information regarding an insertion depth of the device.

13. The device of claim 1, wherein the flattened base comprises a concave surface adjacent to the expandable member.

14. The device of claim 1, wherein an inferior side of the flattened base that is opposite to the expandable member is configured to provide friction between the flattened base and the pelvic wall.

15. The device of claim 1, wherein the expandable member comprises a plurality of chambers.

16. The device of claim 1, wherein the expandable member comprises a balloon, wherein a first portion of the balloon is less distensible than a second portion of the balloon.

17. A method of assisting repositioning a fetal head of a fetus in a pelvic cavity, the method comprising:
 positioning a flattened base between the fetal head of the fetus and against a wall of the pelvic cavity by manipulating a rigid shaft coupled to the flattened base, where the shaft is located outside of the pelvic cavity, the flattened base having an expandable member attached thereto, the expandable member connected to an inflation tube, the inflation tube positioned radially from a longitudinal axis of the rigid shaft, the rigid shaft having an end having a fixed arcuate shape;

expanding the expandable member in a normal direction from the flattened base, such that the expandable member moves the fetal head away from the wall of the pelvic cavity while the flattened base remains in a fixed shape; and manipulating the expandable member using the shaft positioned exterior to the pelvic cavity to assist in displacing the fetal head from the pelvic cavity.

18. The method of claim 17, further comprising repositioning the fetal head with the flattened base when the expandable member is unexpanded.

19. The method of claim 17, wherein expanding the expandable member occurs with a device selected from a syringe, hand pump, pressure bag, or powered pump.

20. The method of claim 17, further comprising using a valve to compress the expandable member at least partially after expanding.

21. The method of claim 17, further comprising controlling the degree of expansion of the expandable member using a pressure relieving valve in fluid communication with the expandable member.

22. The method of claim 17, wherein positioning the flattened base between the fetal head of the fetus and the wall of the pelvic cavity first comprises inserting the flattened base through an insertion site.

23. A fetus delivery assisting device for assisting with the birth of a fetus, the device comprising:

a rigid shaft having a longitudinal axis, at one end of the shaft is a rigid base to which an inflatable balloon is mounted, the one end of the shaft having a fixed arcuate shape;

an inflation tube for providing fluid to inflate the inflatable balloon, wherein the inflation tube is positioned radially from the longitudinal axis of the rigid shaft;

the rigid base and the inflatable balloon are configured to accept a fetal head and where the inflatable balloon is configured to expand in a radial direction away from the longitudinal axis of the rigid shaft;

the inflatable balloon, upon inflation, is configured to displace the fetal head from a pelvic cavity when inflated while pressing the rigid base against a pelvic cavity; and the shaft is configured for manipulating the inflatable balloon to displace the fetal head from the pelvic cavity.

24. The fetus delivery assisting device according to claim 23, wherein the shaft comprises a handle at an end opposite to the rigid base.

25. The fetus delivery assisting device according to claim 24, wherein the handle comprises a widening of the shaft.

26. The fetus delivery assisting device according to claim 23, wherein the shaft has a curved shape.

27. The fetus delivery assisting device according to claim 23, wherein the inflation tube is attached to the shaft.

* * * * *